United States Patent [19]
Zadini et al.

[11] Patent Number: 5,609,586
[45] Date of Patent: Mar. 11, 1997

[54] INTRAVAGINAL EXPANDABLE MEMBER FOR PREVENTION OF VAGINAL BLEEDING

[76] Inventors: Filiberto P. Zadini; Giorgio Zadini, both of 2237 Hilltop La., Camarillo, Calif. 93012

[21] Appl. No.: 425,951

[22] Filed: Apr. 18, 1995

[51] Int. Cl.⁶ .............................. A61F 13/20; A61F 13/15
[52] U.S. Cl. ...................... 604/358; 604/385.1; 604/904; 604/11; 604/15
[58] Field of Search ................... 604/904, 1–3, 604/11–18, 358, 385.1

[56] References Cited

U.S. PATENT DOCUMENTS

| | | | |
|---|---|---|---|
| 1,555,708 | 9/1925 | Gale | 604/904 |
| 2,938,519 | 5/1960 | Marco | 604/904 |
| 3,570,489 | 3/1971 | Brown | 604/904 |
| 3,965,905 | 6/1976 | Schoenholz et al. | 604/904 |
| 3,971,378 | 7/1976 | Krantz | 604/904 |
| 4,374,522 | 2/1983 | Oleusky | 604/904 |
| 5,383,891 | 8/1993 | Walker | 604/904 |

FOREIGN PATENT DOCUMENTS

| | | | |
|---|---|---|---|
| 1123155 | 11/1982 | Canada | 604/904 |
| 493411 | 3/1930 | Germany | 604/904 |
| 1599027 | 10/1990 | U.S.S.R. | 604/904 |

*Primary Examiner*—John G. Weiss
*Assistant Examiner*—Dennis Ruhl
*Attorney, Agent, or Firm*—Robert M. Sperry

[57] ABSTRACT

An intravaginal resiliently expandable member impermeable to fluids providing sealable closure of the vaginal canal for the prevention of exit of blood, including menstrual blood, or other organic fluids from the vaginal orifice. Said intravaginal resiliently expandable member can be used alone or in tandem combination with blood absorbing devices such as intravaginal tampons for the prevention of blood leakage.

17 Claims, 3 Drawing Sheets

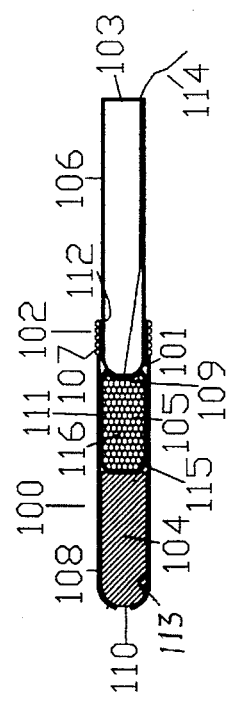
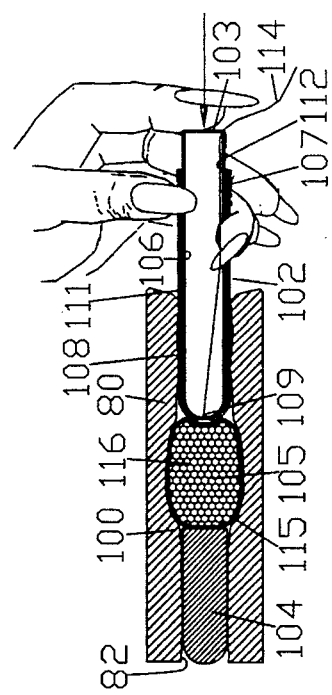
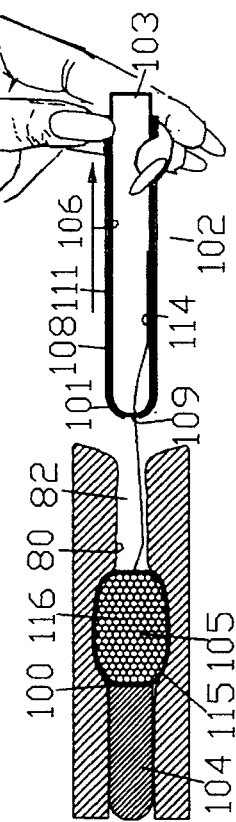
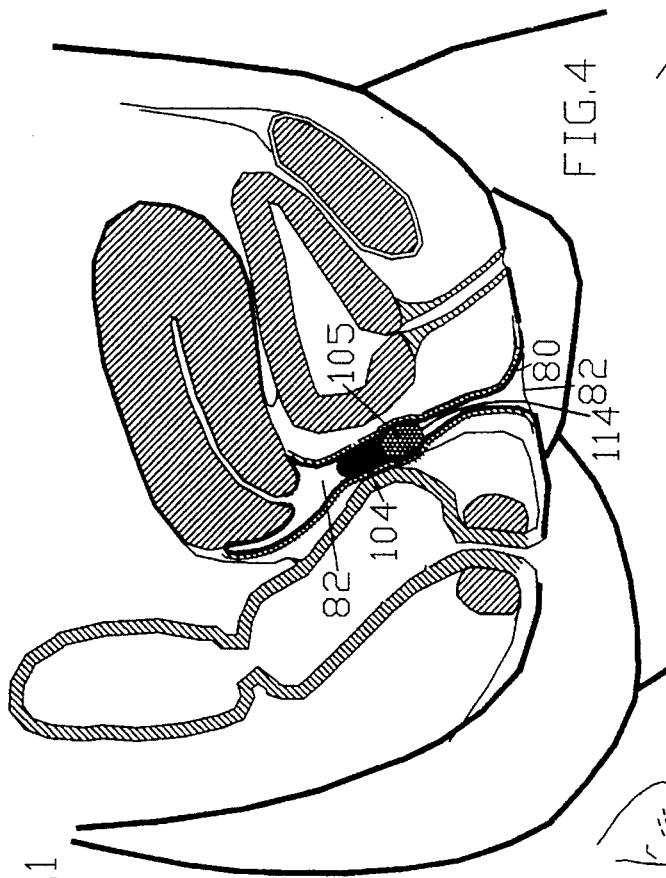
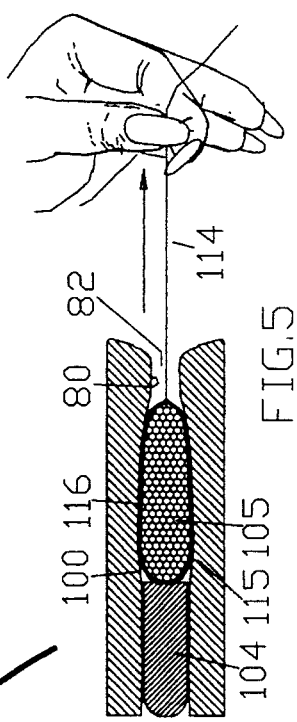

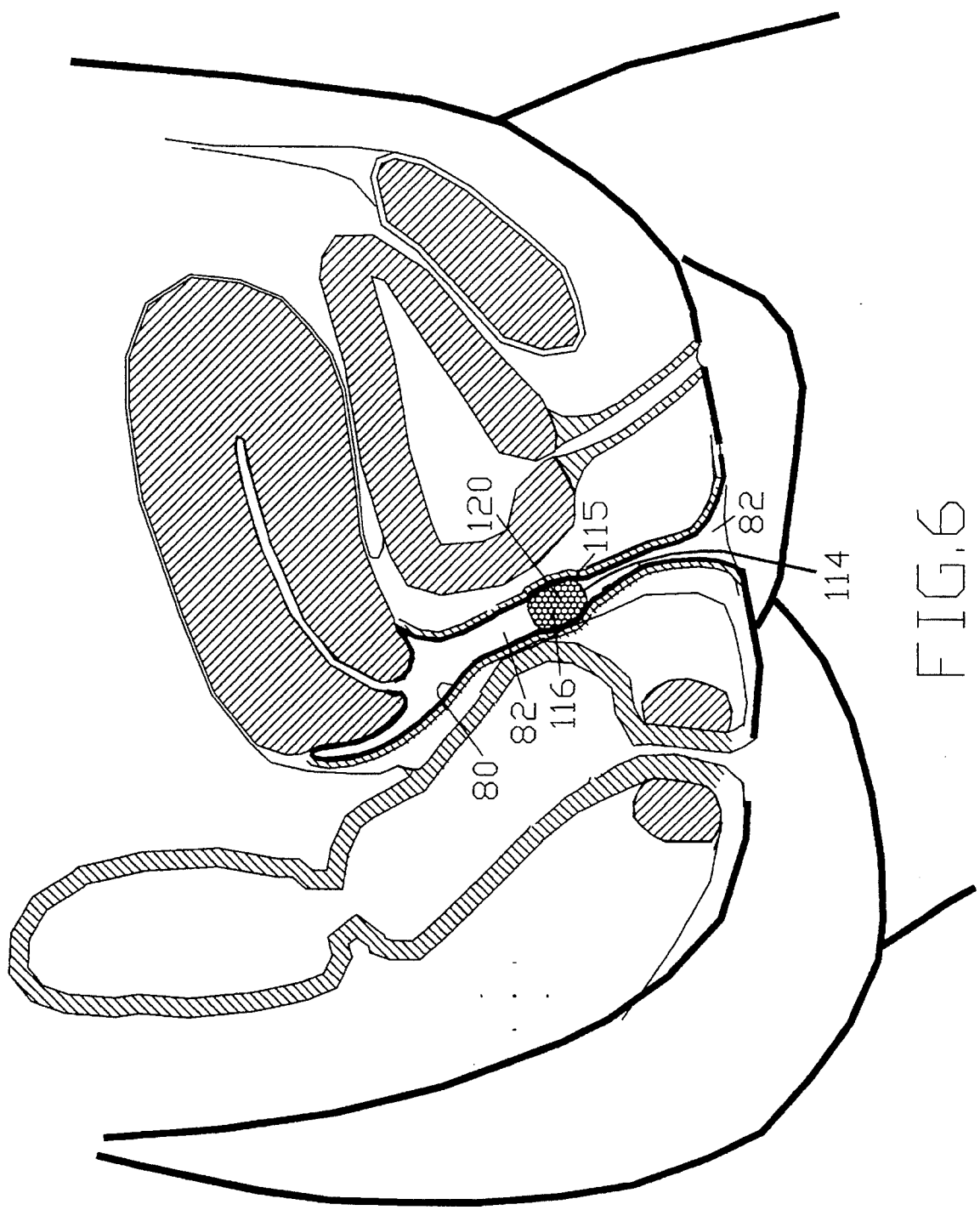

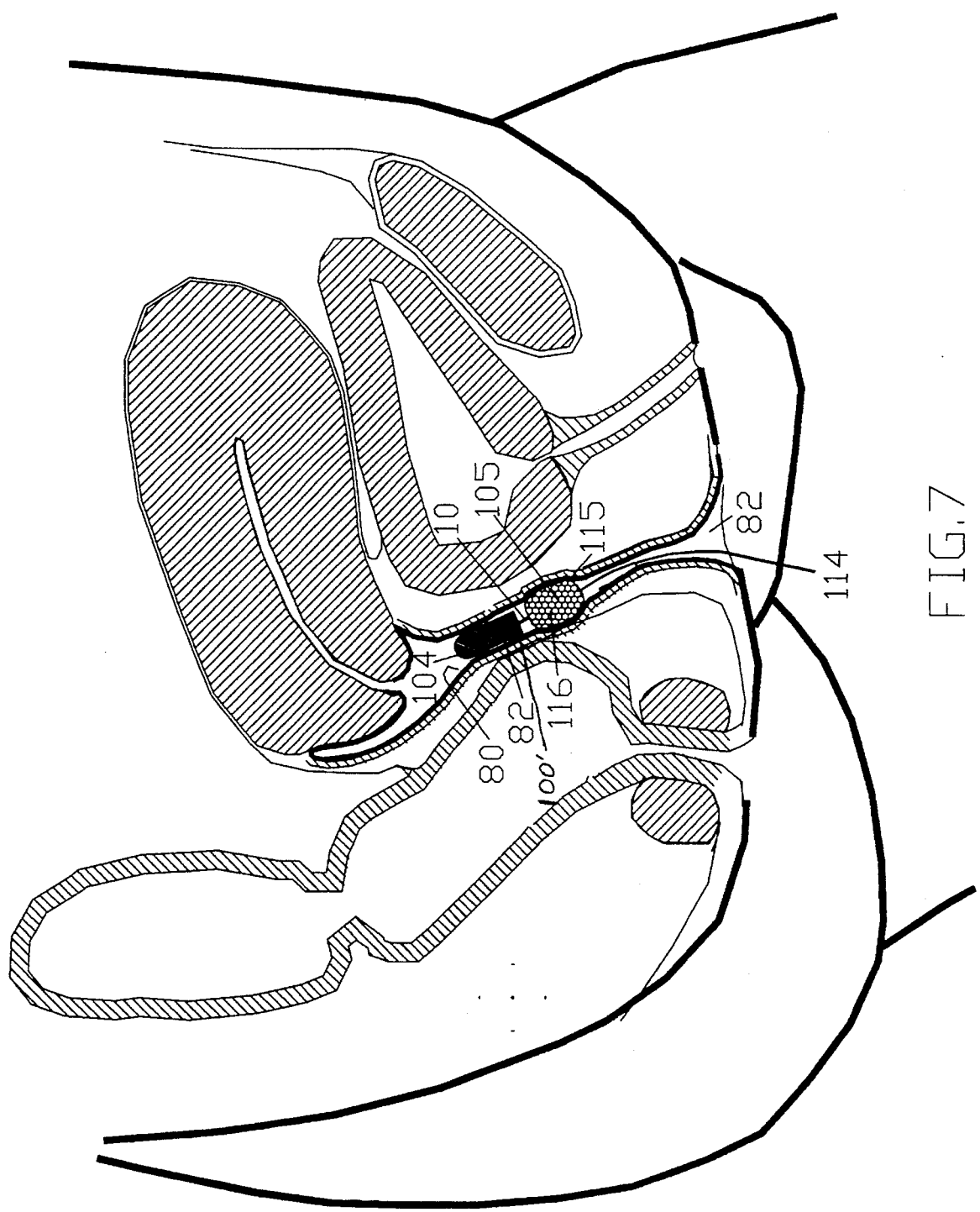

INTRAVAGINAL EXPANDABLE MEMBER FOR PREVENTION OF VAGINAL BLEEDING

FIELD OF THE INVENTION

This invention relates to obstetrical-gynecological devices, more specifically to intravaginal devices apt to prevent leaking or exit of blood or any other organic fluid from the vagina.

BACKGROUND-DESCRIPTION OF THE PRIOR ART

The vagina is a musculomembranous tubular organ extending from the uterine cervix to the exterior of the body. The vaginal canal is about 9 or 10 cm long. Its lumen is generally quite small, and the walls that surround it are usually in contact with each other. Various are the organic fluids which pass through the vaginal canal during the female lifetime, such as blood, vaginal secretion fluids, amniotic fluid, etc.

An important organic fluid passing through the vaginal canal and exiting through the vaginal orifice is blood, either as a result of physiological conditions such as the menstrual period or as a result of pathological conditions such as cervical or endometrial carcinoma or as a result of dysfunctional uterine bleeding. The various inconveniences to women resulting from the occurrence of physiological bleeding occurring during the menstrual period have prompted attempts to regulate or control the outflow of menstrual bleeding according to the women personal and social needs. For the purpose of controlling the outflow of menstrual blood, vaginal tampons were introduced a few decades ago. Vaginal tampons are common catamenial devices made of absorbing material and insertable into the vagina by the female user. Due to their absorbing material, tampons, once inserted into the vagina, begin to absorb upon contact the blood they meet, which outflows from the cervical canal into the vagina, and function as reservoirs aiming at delaying exit of the blood from the vaginal orifice conceivably until they become saturated with blood and, in so doing, they exert a regulatory effect on the outflow of menstrual bleeding to meet women's' needs or preferences.

However, regardless of their absorbency capabilities, tampons, for various reasons, are known to allow leakage of menstrual blood at rather unpredictable time or shortly after insertion, falling short of providing the regulatory effect which is the very reason for their use. No known tampon is capable of preventing leakage of blood from the vaginal orifice, regardless of shape, size, intravaginal resting site, absorbency capabilities of the material or materials of which they are made of, etc. Blood may leak from the vaginal orifice because the tampon is too early saturated with blood or because the blood flow is disproportionately heavy for the absorbency capabilities of the inserted tampon or because the tampon does not provide an adequate sealing with the vaginal walls or orifice or for all the above reasons variously combined.

Despite the use of tampons, therefore, leakage of blood from the vaginal orifice is almost the rule during the days of the vaginal bleeding and its occurrence may result in a great deal of annoyance and inconvenience to the woman: leakage indeed actually defeats the main purpose for which tampons are used.

Prior art deals with the problem of leakage of the tampons, some inventions by providing additional blood reservoirs to the tampons, some others by increasing the tampons absorbing capabilities by the means of improved absorbing material, others by using absorbing pads to apply in correspondence of the vaginal orifice to capture the blood escaped from the tampon. In all such cases, main object of the prior art is rather to minimize and possibly delay the outflow of blood, rather than reliably preventing the leakage of blood until it is the appropriate time for the woman, as determined by the woman rather than by her endometrium, to permit exit of the menstrual blood from the vaginal orifice.

The invention by R. Poncy et Al., U. S. Pat. No. 4,020,841, discloses a catamenial tampon comprising an elongated core of conventional highly absorbent fibrous material enclosed along its sides and posterior end by a sheath of nonabsorbent, resilient and thus compressible foam material whereby the storage capacity of the absorbent core is unaffected by compressive forces due to muscular activity or withdrawal of the tampon, such compression being accommodated fully by said nonabsorbent outer sheath.

The catamenian device by R. Poncy is therefore a tampon where the absorbing material, an elongated core, is nested almost entirely in a cup-like sheath which exposes only the anterior end of the tampon. Said cup-like sheath acts also as a cushion interposed between the tampon and the vaginal walls.

One of the most significant drawbacks of Poncy's device is the fact that, in order to expand sufficiently to extend from wall to wall of a vagina to effect sealing and prevent leakage of blood, the sheath of resilient material which envelops the tampon along its sides needs to be conveniently thick. Such a need for sufficient thickness of the sheath necessarily requires that the tampon core nested within the sheath be constructed of a significant smaller diameter than any conventional tampon made to fit the vaginal canal. In terms of volume, the volume of the absorbing core proposed by Poncy is necessarily a small fraction of the volume of any conventional tampon. Since the volume of a tampon is a key factor influencing its absorbing capacity, the absorbing capacity of the tampon proposed by Poncy is necessarily a small fraction of the absorbing capacity of any conventional tampon. Such a drawback, combined with the significantly reduced exposure of the absorbing surface of the tampon, confined to the anterior end of the tampon, leads to the great inconvenience of defeating the fundamental function of a tampon, which is of delaying the menstrual flow as a result of its absorption of blood. Due to its reduced absorbing capacity, the Poncy's catamenian tampon, therefore, has the very undesirable disadvantage of requiring more frequent replacements, as compared to the number of replacements required with a conventional tampon made of the same material because of the restriction of volume expansion undergone by Poncy's tampon due to the presence of the resilient material surrounding the actual tampon core, or, conversely, Poncy's tampon has the inconvenience of causing the inconvenience of gushing of blood upon removal of the device, if the device is left in place longer than allowed by its absorbing capacity.

Of course, a tampon requiring to be frequently replaced loses greatly or entirely its usefulness.

It is obvious, therefore, that, in order to attain certain advantages over the conventional tampons, the Poncy's device inevitably belittles the most essential function of a tampon, i.e. its absorbing capacity.

In addition to significantly impairing the capacity of absorption of a tampon, the arrangement of the resilient material all around the tampon, as disclosed by Poncy et Al., also affects the overall expandability of the resilient material, because the resilient material in Poncy's disclosure does not extend full thickness from wall to wall of the vagina but is significantly reduced in thickness due to the intermission of a substantially non-compressible tampon: given the wide range of anatomical variability in vaginal size, such restriction in expandability may result with less than optimal vaginal sealing and may result with poor blood leakage prevention.

The surrounding of the tampon by the sheath of resilient material, particularly along the sides of the tampon, as disclosed by Poncy, is not preferential nor exemplificatory in Poncy's patent, but it clearly represents the very essence of Poncy's invention, being the only arrangement conceivably possible to achieve all the objectives of Poncy invention. In addition to the objective of preventing blood leakage, the sheath surrounding the tampon obviates the apparent problem of susceptibility to compression of conventional tampons, which, according to the inventors of said device, is a reason for reduction of the effectiveness of the tampon to retain or store the menstrual fluids, inasmuch compression of the tampon could result in the discharge of accumulated fluids both when the tampon is compressed directly such as during withdrawal or indirectly due to the increase in intravaginal pressure caused by the most common of body movements. Also the objective of obviating to the irritation of the vaginal mucosa resulting from frequent insertion and withdrawal of tampons during periods of heavy menses flow can only be attained by a sheath enveloping the tampon core along its sides. A sheath enveloping the tampon core along its sides is, according to its inventors, also essential to obviate to the chafing which may occur during periods of light menses flow because of the tendency of the tampon to absorb whatever small amount of liquids are present on the vaginal walls thereby generating excess friction between the tampon and the vaginal walls.

Zadini et At. describes in their patent application Ser. No. 08/391,342 an inflatable intravaginal device for prevention of blood leakage from the vagina orifice. Such a device expands by inflation not by resiliency.

BRIEF SUMMARY OF THE INVENTION

The present invention comprises an intravaginal expandable member impermeable of, substantially impermeable to fluids, which by resiliency self-expands from wall to wall of a vagina obliterating the space between said expandable member and the vaginal walls, preventing passage of blood. Said expandable member has a shape such as it precludes housing of bodies of non-resilient material within said expandable member, so as to maximize its expandability by resiliency. Such an expandable member is capable of providing reliable vaginal closure to outflow of organic fluids such as menstrual blood from the vaginal orifice until the woman determines to be the appropriate time for allowing exit of the menstrual blood from the vaginal orifice, and also provides reliable vaginal closure to pathological bleeding or dysfunctional uterine bleeding. Vaginal closure is attained by the expandable member especially on account of its easy self-adaptability to the variability of size and shape of the vaginal lumen granted by its ability to expand without interposed obstacles.

Also the expandable member easily adapts to the variability of smoothness of the vaginal walls, and expands to exert a gentle pressure on the vaginal mucosa, such a pressure being sufficient to prevent passage of blood between the expandable member itself and the vaginal mucosa. The device may be used alone, as a stand-alone intravaginal device, or may be used in combination with blood absorbing means such as tampons, being arranged in tandem position. When combined with tampons, due to its peculiar position in respect to the tampon, i.e. a tandem position, the expandable member has the peculiarity of leaving all the essential properties of a tampon, including volume, exposed absorbing surface, tampon susceptibility of expanding upon absorption of blood, substantially unaltered by said tandem combination. When used as a stand-alone device, for instance in cases of pathological or dysfunctional vaginal bleeding, the expandable member, being impermeable or substantially impermeable to fluids and expanding to exert pressure on the vaginal mucosa, prevents passage of blood between the expandable member and the vaginal mucosa.

OBJECTS OF THE INVENTION

It is an object of the present invention to propose a device that conceivably offers a reliable and practical solution to the problem of vaginal bleeding, in particular to the problem of untimely leakage of menstrual blood. As such, i.e. if employed as a means for prevention of leakage of menstrual blood, the device that we propose can be used in combination with blood absorbing material, such as tampons. When associated with a conventional tampon, our device will reliably prevent untimely leakage of menstrual blood while offering the unique property of preserving, at the same time, the absorbing capacity of the conventional tampon unaltered along with all the other characteristics of the tampon.

The device that we propose, however, may also be used alone to provide means for preventing vaginal bleeding in the event of pathological or dysfunctional vaginal bleeding, in substitution of the traditional vaginal packing, which is notoriously scarcely effective.

It is another object of the present invention to offer a device capable of assuring prevention of blood leakage regardless of the anatomical size, shape, changes of direction, lumen and contour of the vagina, as a result of the device remarkable adaptability to anatomical size, shape, contour of the vagina, and its adaptability to contingent changes of size, shape, lumen contour of the vagina, in order to maintain its outer surface in close contact with the vaginal mucosa and offer a sealing closure to blood in any condition. Such a remarkable adaptability is partially a result of the fact that our device is resilient from vaginal wall to vaginal wall, being structurally free from intermissions of non-resilient material which would inevitably decrease its expandability.

It is another object of this invention to propose an expandable member, capable of reliably achieving prevention of leakage of menstrual blood while being easy to be worn, conceivably adding no discomfort to the female user, by gently applying upon the vaginal mucosa a pressure just barely sufficient to prevent passage of blood between the device and the vaginal mucosa, such a pressure being generally proportional to the pressure, notoriously negligible, exerted by menstrual blood.

It is another object of this invention to propose an expandable member, capable of reliably achieving prevention of leakage of menstrual blood, while being easy to insert and likewise easy to extract.

It is an other object of the present invention to provide an intravaginal device capable of preventing, when indicated, leakage or outflow, in any amount, of organic fluids in general, besides blood, from the vaginal orifice.

It is an object of the present invention to provide an expandable member, offering means of prevention of significant hemorrhage in cases for instance of pathological bleeding, by reliably preventing excessive blood loss from the vagina, by limiting the amount of blood extravasation to an amount not exceeding the maximum capacity of reservoir of a tract of the vagina proximal to the site of placement of said expandable device, as a result of a blockage exerted by such expandable intravaginal device on the vaginal transit of blood. A device of this kind may prevent the serious medical complications associated with massive vaginal-uterine bleeding and at times may well be a life saving device. If used for that purpose, it will be used as a substitute for the traditional vaginal packing, notoriously scarcely effective.

DRAWING FIGURES

FIG. 1 shows the expandable member in tandem combination with a conventional tampon, mounted within an applicator.

FIG. 2 shows the tampon-expandable member assembly of FIG. 1 after insertion into the vagina, and expansion of the expandable member after ejection from the applicator within the vagina.

FIG. 3 shows removal of the applicator from the vagina with the tampon-expandable member assembly left in situ.

FIG. 4 shows a cross section view of the female pelvis with the tampon-expandable member assembly resting in vagina and providing sealable closure of the vaginal canal.

FIG. 5 shows the tampon expandable member assembly of FIG. 1 being extracted from the vagina by the user's hand via a string.

FIG. 6 illustrates expandable member of FIG. 1 alone, without a tampon, shown in situ in the vaginal canal in a cross section view of the female pelvis.

FIG. 7 shows another embodiment of the tampon-expandable member assembly of FIG. 1 wherein the connection between tampon and expandable member is achieved via a string.

DETAILED DESCRIPTION OF THE INVENTION

A typical embodiment of the invention is illustrated in FIG. 1. The device, generally indicated at 100, is composed of expandable member 105 and of tampon 104. Expandable member 105 is positioned in a tandem position in respect of tampon 104. As such, sides walls 113 of tampon 104 are substantially free from contact with expandable member 105. Expandable member 105 is impermeable or substantially impermeable to fluids, and expands as a result of the resiliency of the material is made of, rather than expanding by absorption of fluids such as blood, as in the case of a tampon.

FIG. 1 shows the tampon-expandable member generally indicated at 100 mounted within applicator 102. Applicator 102 of generally cylindrical hollow shape is composed of outer member 108 and inner member 106, both of substantially rigid material for example cardboard. Outer member 106 containing tampon-expandable member assembly 100, has anterior opening 110 and posterior opening 112. Inner member 106 is telescopically mounted within posterior segment 107 of outer member 108. Tampon 104 is made of suitable absorbable material while expandable member 105 has the physical characteristics of being of a resilient structure 116 and has impermeable or substantially impermeable surface 115. Expandable member 105 is slideably mounted, in a contracted, compressed status within outer member 108 of applicator 102, being constrained within outer member 108 by substantially rigid walls 111 of outer member 108. String 114 is attached to expandable member 105, entering hollow inner member 106 through hole 109 formed in anterior end 101 of inner member 106 and exiting through posterior end 103 of inner member 106 of applicator 102.

The expandable member, 105, is compressed within the rigid walls 111 of outer member 108 of applicator 102, and expands by resiliency upon ejection from applicator 102 within vagina 82 of FIG. 4. Upon expansion, expandable member 105 exerts a pressure upon vaginal walls 80, FIG. 2, providing sealable closure of the vaginal canal 82, FIG. 2. The structure 116 of resiliently expandable member 105 can be various: foamy, spongy, trabecular, porous, microporous, cellular, solid compressible, of interwoven fibers and others. The material can be any suitable resilient material such as rubber, silicone, latex, polyurethane, neoprene, polyethylene, polystyrene, polyvinyl, polymide or other polymers, or any material which can be compressed and self-decompresses.

Regardless of the material, density or structure, expandable member 105 is impermeable or substantilly impermeable to fluids, and in particular to blood. Resiliently expandable member 105 can alternatively be enveloped within a thin layer of impermeable or substantially impermeable material.

In use, applicator 102 containing tampon-expandable member 100 is inserted into vaginal canal 82 by the user. As shown in FIG. 2, once inserted in vagina canal 82, inner member 106 is pushed forward with one or more fingers by the user hand, while outer member 108 is firmly held with the other fingers. Advancement of inner member 106 of applicator 102 in respect of outer member 108 will cause ejection of tampon-expandable member assembly 100 from outer member 108 through its anterior opening 110. As soon as ejected from outer applicator member 108 through opening 110, expandable member 105, being no longer constrained within the relatively rigid side wall 111 of outer member 108, will rapidly expand so that its outer impermeable or substantially impermeable surface 115 will become in contact with vaginal wall 80 and will exert a sufficient pressure to not permit passage of blood between vaginal walls 80 and expandable member outer surface 115, providing, in such a way, a sealable closure of vaginal canal 82. While tampon 5104 will provide absorption for blood, expanded expandable member 105 will prevent vaginal exit of the blood which has escaped absorption.

FIG. 3 shows tampon-expandable member 100 resting in vagina 82 while applicator 102 is being extracted from vagina 82. FIG. 4 shows the tampon-expandable member assembly resting in vagina 82, in a cross section view of the female pelvis. Expanded expandable member 105 provides sealable closure of vaginal canal 82.

In FIG. 5, tampon-expandable member 100 is extracted from vagina 82 by the user's hand pulling on string 114. Expandable member 105 will elongate due to its resilient nature facilitating its exit from vaginal canal 82.

FIG. 6 shows resilient expandable member 120 as a stand-alone device, not in combination with blood absorbing means such as tampon 104 described in FIG. 1 through 5. Resilient expandable member 120 is used in the same way as expandable member 105 of FIG. 1 through 5. While outside the vaginal canal, expandable member 120 is maintained in a contracted status, not being allowed to expand, by the relatively rigid walls of the outer member of the applicator. Once inserted in vagina and ejected from the applicator, resilient expandable member 120 will self-expand due to its resiliency. As shown in FIG. 6 expandable member 120, once fully expanded, with its impermeable or substantially impermeable surface 115 in contact with vaginal walls 80 will provide sealable closure of vaginal canal 82. In this embodiment, blood will freely accumulate unabsorbed above the obstruction caused by expanded expandable member 120, due to the lack of any absorbing tampon..

FIG. 7 shows another embodiment generally indicated at 100' of the tampon-expandable member 100 described in FIG. 1 through 5. In this form, tampon 104 and expandable member 105 still arranged in a tandem position are not in contact with each other, but are connected via connecting means such as string 10. Mode of use and function are exactly the same as the ones described for tampon-expandable member assembly 100 of FIG. 1 through 5.

What we claim is:

1. A catamenial device for insertion into a vaginal canal having a wall, said device comprising:

a first member which is absorbent; and a second member for sealingly engaging said wall of said canal, said second member being substantially fluid impermeable and connected in tandem with said first member, said second member being resiliently expandable from a first state having a first diameter to a second state having a second diameter, said second diameter being greater than a diameter of said first member.

2. The device of claim 1 wherein:

said second member is free of contact with said first member and is connected to said first member via a connecting member.

3. The device of claim 1 wherein:

said second member is in contact with said first member.

4. The device of claim 1 further comprising:

means for removing said members from a vagina.

5. The device of claim 1 wherein:

said second member is expandable to prevent fluids in said vaginal canal from leaking about said second member.

6. The device of claim 1 wherein:

said second member has a substantially impermeable surface.

7. The device of claim 1 wherein said resilient member includes a foam structure of a resilient material.

8. The device of claim 1 wherein said resilient member includes a substantially spongy structure of a resilient material.

9. The device of claim 1 wherein said resilient member includes a substantially trabecular structure of a resilient material.

10. The device of claim 1 wherein said resilient member includes a substantially cellular structure of a resilient material.

11. The device of claim 1 wherein said resilient member includes a substantially porous structure of a resilient material.

12. The device of claim 1 wherein said resilient member includes a structure of intertwined fibers of a resilient material.

13. The device of claim 1 wherein said resilient member includes a solid compressible structure of a resilient material.

14. The device of claim 1 wherein said resilient member includes a foam rubber compound.

15. The device of claim 1 wherein said resilient member includes a silicone compound.

16. A catamenial device for insertion into a vaginal canal having a vaginal wall, said device comprising:

a blood-absorbent member of a generally cylindrical shape, said blood-absorbent member having a side wall, and a substantially fluid-impermeable member for sealingly engaging said wall of said canal, said substantially fluid-impermeable member being resiliently expandable from a first state having a first diameter to a second state having a second diameter, said second diameter being greater than a diameter of said blood-absorbent member, said substantially fluid-impermeable member being in contact with said blood-absorbent member and leaving a substantial portion of said side wall of said blood-absorbent member exposed for blood absorption.

17. A catamenial device for insertion into a vaginal canal having a vaginal wall, comprising:

an intravaginal blood-absorbent member, and a substantially fluid-impermeable member for sealingly engaging said wall of said canal, said substantially fluid-impermeable member being resiliently expandable from a first state having a first diameter to a second state having a second diameter, said second diameter being greater than a diameter of said intravaginal blood-absorbent member, said substantially fluid-impermeable member being connected to said intravaginal absorbent member and leaving cephalad a substantial portion of said intravaginal absorbent member exposed for blood absorption.

\* \* \* \* \*